(12) United States Patent
Hickey et al.

(10) Patent No.: US 6,485,730 B1
(45) Date of Patent: Nov. 26, 2002

(54) SINGLE SERVING PARAFFIN TREATMENT SYSTEM AND METHOD

(75) Inventors: Beth Ann Barrick Hickey, Arlington, TX (US); Rebecca Phillips Gentry, Ovilla, TX (US); Royce E. Gentry, Ovilla, TX (US)

(73) Assignee: E.O.H. Industries, Inc., Arlington, TX (US)

( * ) Notice: Subject to any disclaimer, the term of this patent is extended or adjusted under 35 U.S.C. 154(b) by 0 days.

(21) Appl. No.: 09/708,938

(22) Filed: Nov. 8, 2000

Related U.S. Application Data
(60) Provisional application No. 60/164,185, filed on Nov. 9, 1999.

(51) Int. Cl.[7] .............................. A61K 9/00; A61K 7/00; A61K 7/04; A61K 7/48
(52) U.S. Cl. ..................... 424/400; 424/401; 424/70.1; 514/886; 514/887
(58) Field of Search ................................ 424/70.1, 400, 424/61; 514/886, 887; 206/538, 438, 561

(56) References Cited

U.S. PATENT DOCUMENTS

| | | |
|---|---|---|
| 2,463,329 A | 3/1949 | Stansbury |
| 3,157,774 A | 11/1964 | Moore |
| 4,149,536 A | 4/1979 | Villard |
| 4,632,115 A | 12/1986 | Bernardini |
| 4,696,303 A * | 9/1987 | Bernardini ............... 128/402 |
| 4,782,835 A * | 11/1988 | Bernardini ............... 128/402 |
| 4,880,415 A | 11/1989 | Urakami |
| 4,964,402 A | 10/1990 | Grim |
| 5,143,064 A | 9/1992 | Cochran |
| 5,674,268 A | 10/1997 | Riazi |

OTHER PUBLICATIONS

Profiles—Advertising on package for Professional Manicure Warmer, Model 8574, distributed by Belson Products, 1997.

* cited by examiner

*Primary Examiner*—Thurman K. Page
*Assistant Examiner*—Rachel M. Bennett
(74) *Attorney, Agent, or Firm*—John G. Fischer, Esq.; Storm & Hemingway, L.L.P.

(57) ABSTRACT

A single serving paraffin treatment system and method of application is disclosed which includes the steps of heating a small quantity of paraffin above its melting temperature, applying the paraffin to the hand or foot with a brush. The paraffin is contained in individualized disposable containers which are receivable in a heating unit. The heating unit preferably has at least two temperature settings.

18 Claims, 3 Drawing Sheets

SINGLE SERVING PARAFFIN TREATMENT SYSTEM AND METHOD

CROSS-REFERENCE TO RELATED APPLICATION

Provisional Application Serial No. 60/164,185 filed Nov. 9, 1999.

BACKGROUND OF THE INVENTION

1. Technical Field

This invention relates generally to paraffin treatments as used in the beauty industry, and in particular to a new method and apparatus for application of a single serving of paraffin in manicure and pedicure treatments.

2. Background Information

Paraffin application to the skin is well known as a therapeutic treatment with results including moisturizing, smoothing, hydrating, and lightening. It is also well known to treat hands and feet by dipping them in a bath of melted paraffin.

Prior paraffin treatment systems were designed for multiple salon use. Most salons use a unit that has, a large enough container to hold six pounds of paraffin, and a heating unit for melting the paraffin. The units are large because the container must be large enough to accommodate a person with large hands, or feet, and must include allowance for displacement of the paraffin by the person's extremity, without overflowing the container. To start these units, they must be turned on and placed at a melt setting. Paraffin generally melts between approximately 52° and 63° Centigrade (126° and 145° Fahrenheit). Purified topical paraffin mixtures typically melt between approximately 48° and 51° Centigrade (118° and 123° Fahrenheit). Topical paraffin products may contain other components such as mineral oil, coconut oil, lanolin, clay, coloring, and other ingredients. The presence of various ingredients in various ratios will affect the melting temperature of the product. At the melt setting, the blocks of paraffin will commonly take four to five hours to melt to a usable state. The slow melt is a result of the large quantity of paraffin used, the large container volume, the need to avoid vaporization and burning of the paraffin, and safety considerations that prohibit high temperature melting that could burn a consumer. The paraffin must be completely melted. At the melt temperature setting, the paraffin is too hot to use, so the unit is then set at an operational setting which allows the paraffin to cool to a useable temperature that is still in the liquid state. The long start up time requires the unit to be left on continuously, twenty-four hours a day, seven days a week in a commercial use setting. Once in use, the same paraffin supply will be used to treat the hands of numerous clients. The paraffin for use in hand and foot treatments is typically shipped in a six-pound block or in six one-pound blocks. The blocks or bags of paraffin are subjected to high temperatures inside common carrier vehicles, which can cause the paraffin to melt. Truck containers can reach summer time temperatures in excess of 120° Fahrenheit. To prevent the paraffin from leaching or running outside of their shipping containers, paraffin products are normally packaged in barrier bags. Barrier bags are, made of a thick and durable plastic. The bags are flexible and typically heat-sealed.

Non-paraffin manicure warmers are well known. These units are smaller, and are designed to warm manicure lotions for dipping the ends of the fingers in. One such product is the Model 8574 Professional Manicure Warmer distributed by Belson Products, located in Miami Lakes, Fla. These products may include the use of disposable lotion cups.

One disadvantage of the prior art is that the units used are too large to be practical for small salon, kidsk, booth, or home use. Another disadvantage of the prior art is that the units used are too expensive to be practical for small salon, kiosk, booth, or home use. Another disadvantage to the prior art is that the units require a long start-up time to melt the paraffin. Another disadvantage of the prior art is that the units must be left on at all times for commercially practical use. Another disadvantage of the prior art is that they require the use of a large quantity of paraffin, regardless of how many hand treatments are desired. Another disadvantage to the prior art is that multiple users are exposed to residual skin debris and body fluids of the previous users. Another disadvantage to the prior art is that it wastes paraffin and electricity. Another disadvantage to the prior art is that they are difficult to clean.

Thus, it is seen that there is a need for an improved system for paraffin treatments as applied to the hands and feet that addresses the issues identified above.

BRIEF SUMMARY OF THE INVENTION

A primary advantage of the present invention is that it incorporates the use of a compact heating unit that is small enough to be practical for small salon, kiosk, booth, or home use. Another advantage of the present invention is that it incorporates the use of inexpensive heating units and smaller material quantities such that the economics of operation are practical for small salon, kiosk, booth, or home use. Another advantage of the present invention is that the heating units and material quantities require a dramatically reduced start-up time to melt the paraffin. Another advantage of the present invention is that the heating units can be shut off, even under conditions of commercial use. Another advantage of the present invention is that it uses a smaller quantity of paraffin, and a smaller quantity of paraffin for each application, and only enough for the number of applications required. Another advantage of the present invention is that multiple users are not exposed to residual skin debris and body fluids of previous users. Another advantage of the present invention is that it conserves raw materials (paraffin) and electricity. Another advantage of the present invention is that the system is easy to clean. Another advantage of the present invention is that a paraffin mass sufficient for a treatment can be shipped in the container for which it will actually be used, making up a single-serving "paraffin charge."

Other advantages of the present invention will become apparent from the following descriptions, taken in connection with the accompanying drawings, wherein, by way of illustration and example, an embodiment of the present invention is disclosed.

In one embodiment of the present invention, a single-serving paraffin treatment method is disclosed comprising the steps of:

1. melting the paraffin in a container;
2. inserting a brush into the melted paraffin;
3. brushing the paraffin onto a person's hands or feet.

In another embodiment of the present invention, a single-serving paraffin treatment system is disclosed, having a heating unit with a reservoir, a container insertable into the reservoir, a paraffin mass located in the container, and a brush for application of the paraffin. In another embodiment, the brush is made of goat hair. In another embodiment, the brush is made of pony hair. In another embodiment, the container has an upper edge extending above the reservoir of the heating unit to facilitate handling.

In another embodiment of the present invention, a single-serving paraffin charge is disclosed for use in a single-serving paraffin treatment system having a heating unit with a reservoir. The single-serving paraffin charge has a disposable container insertable into the reservoir, a paraffin mass located in the container, and a sealed, removable lid. In another embodiment, the container has a double-wall construction. In another embodiment, the lid is threadedly connected to the container, forming a pressure-sensitive seal between the lid and the container. In another embodiment, a heat-sensitive adhesive seals the lid to the container. In another embodiment, the paraffin mass weighs less than approximately six ounces.

BRIEF DESCRIPTION OF THE SEVERAL VIEWS OF THE DRAWING(S)

The drawings constitute a part of this specification and include exemplary embodiments to the invention, which may be embodied in various forms. It is to be understood that in some instances various aspects of the invention may be shown exaggerated or enlarged to facilitate an understanding of the invention. A reference to and brief description of each figure in the drawing(s) as set forth in 37 CFR 1.74.

DETAILED DESCRIPTION OF THE INVENTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

The steps disclosed for use in a single-serving paraffin treatment method are as follows:

1. melting paraffin in a container;
2. inserting a brush into the melted paraffin;
3. brushing the paraffin onto a person's hands or feet.

Figure 1:
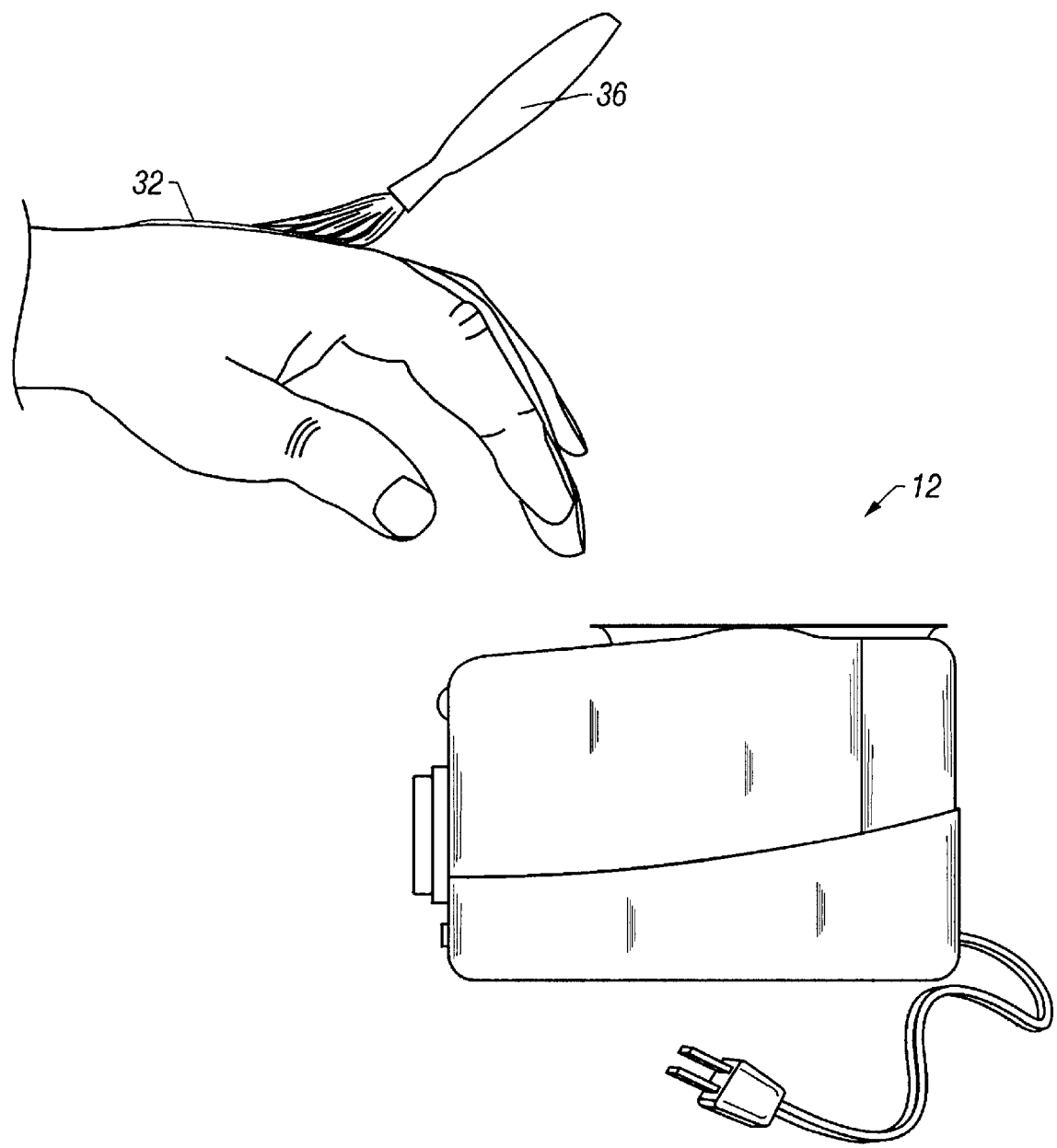
FIG. 1 is an isometric view of the application of the single-serving treatment method of the present invention.

In FIG. 1, the third step of the single-serving paraffin treatment method is shown.

Figure 2:
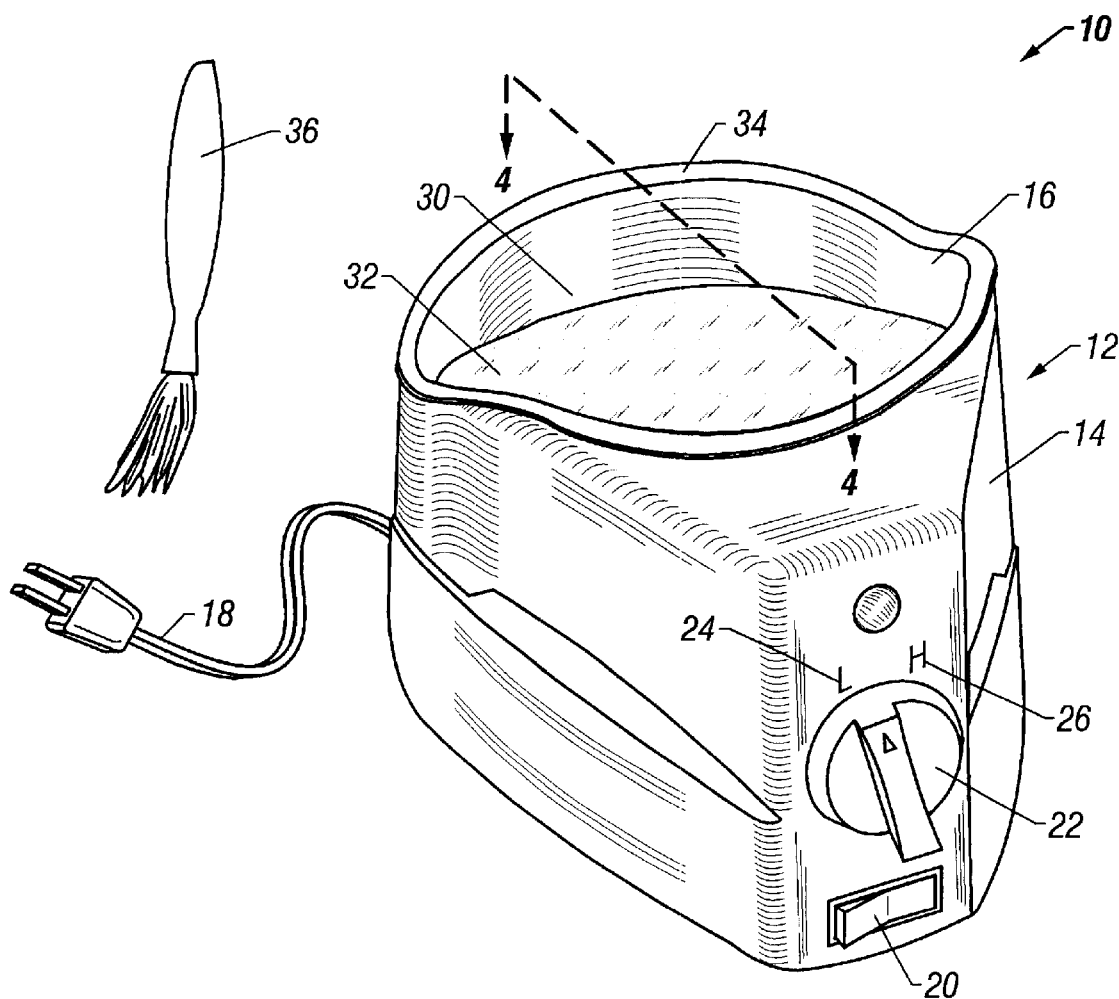
FIG. 2 is an isometric view of the single-serving treatment system of the present invention.

FIG. 2 is a diagram of a single-serving paraffin treatment system 10 of the present invention, shown generally. Treatment system 10 includes a small heating unit 12, as is known to the industry for use in heating lotions for manicures. Heating unit 12 has a body 14 with a reservoir 16. A power cord 18 is adaptable to the available power source of the region in which the device is being used. An on-off power switch 20 transmits power from power cord 18 to heating unit 12. In a preferred embodiment, a temperature control switch 22 selects between a lower temperature setting 24 and a higher temperature setting 26. A container 30 is removably insertable into reservoir 16. Container 30 contains a paraffin mass 32. In a preferred embodiment, paraffin mass 32 weighs between approximately 3 ounces and 6 ounces. In another embodiment, an upper edge 34 of container 30 extends above reservoir 16 to facilitate handling of container 30. In another embodiment, container 30 is disposable. A brush 36 is provided for application of paraffin 32 when melted. In one embodiment, brush 36 is made of goat hair. In another embodiment, brush 36 is made of pony hair.

Figure 3:
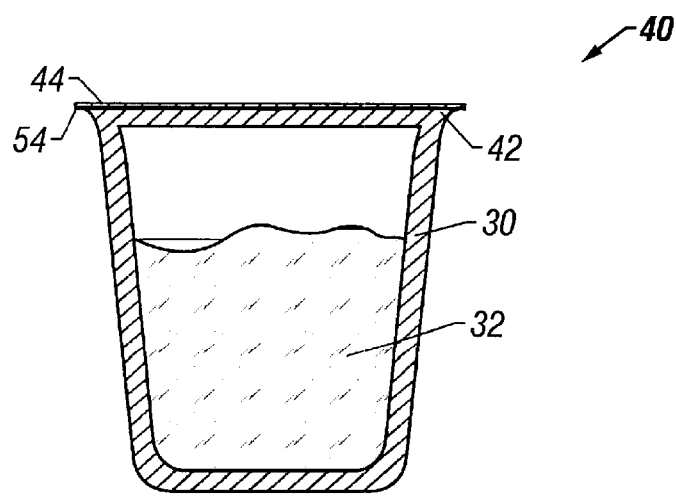
FIG. 3 is a cross-sectional side view of the paraffin charge assembly of the present invention.

FIG. 3 discloses a single-serving paraffin charge 40 generally, for use in single-serving paraffin treatment system 10 having a heating unit 12 with a reservoir 16 as shown generally in FIG. 2. A disposable container 30 is removably insertable into reservoir 16. Container 30 contains a paraffin mass 32. In a preferred embodiment, paraffin mass 32 weighs between approximately 3 ounces and 6 ounces. In another embodiment, an upper edge 42 of container 30 extends above reservoir 16 to facilitate handling of container 30. A lid 44 removably seals against upper edge 42 of container 30. In this embodiment, paraffin mass 32 is sealing contained with container 30, and is thus suitable for both shipping and end use by removal of lid 44. In another embodiment, container 30 is made of a polyvinyl-chloride (PVC) material. In another embodiment, container 30 is made of a polypropylene material.

Figure 4:
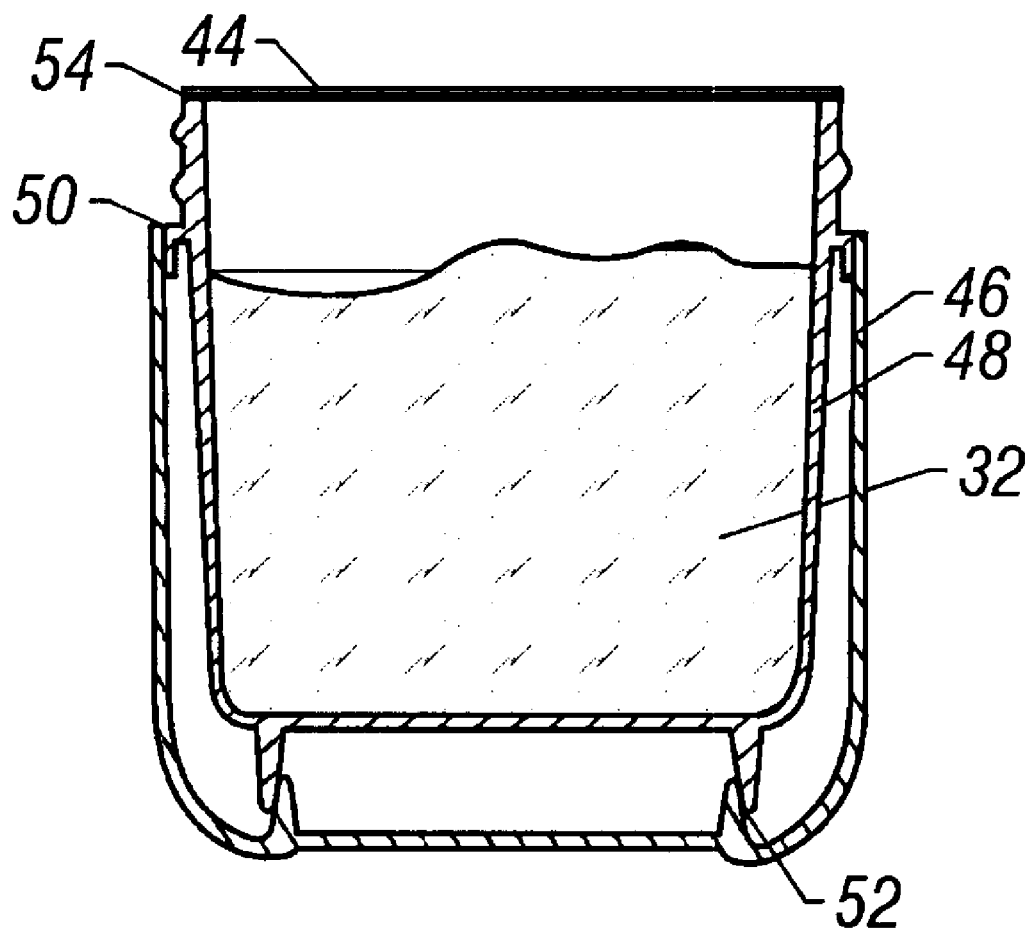
FIG. 4 is a cross-sectional side view of a double-walled paraffin charge assembly of the present invention.

FIG. 4 is a cross-sectional side view of a double-walled paraffin charge assembly of the present invention. In this embodiment, container 30 has a doubled wall structure, including a first wall 46 and a second wall 48. First wall 46 is circumferentially attached to second wall 48 at first interface 50. In another embodiment, first wall, 46 is also circumferentially attached to second wall 48 at second interface 52. In one embodiment, container 30 may be removably attached to lid 44 by a threaded connection. In this embodiment, lid 44 is sealed to container 30 by pressure. In another embodiment, an adhesive 54 is located between lid 44 and upper edge 42 of container 30. In a more preferred embodiment, adhesive 54 is a pressure sensitive adhesive. In another preferred embodiment, lid 44 is coated with a varnish-type coating 56 that when heated becomes sticky and seals against upper edge 42 of container 30.

OPERATION OF THE INVENTION

In a preferred embodiment of the present invention, paraffin 32 is melted in container 30 by a heating unit 12. When paraffin 32 is melted, brush 36 is inserted into paraffin 32 in container 30. With paraffin 32 on brush 36, brush 36 is used to apply paraffin 32 to the hands or feet of the treatment recipient.

In another preferred embodiment of the present invention, container 30 having paraffin 32 is placed in reservoir 16 of heating unit 12. Power switch 20 is turned on. In a preferred embodiment, temperature control switch 22 is selected to higher temperature setting 26 until paraffin 32 melts. When paraffin 32 is melted, lower temperature setting 24 may optionally be selected. With paraffin 32 melted, brush 36 is used to apply paraffin 32 to the hands or feet of the person receiving the paraffin treatment. In one embodiment, brush 36 is made of pony hair. In another embodiment, brush 36 is made of goat hair. Tests performed by the inventors have determined that these brush types worked very well in application of melted topical paraffin to skin. It is common practice in paraffin treatments to enclose the hands or feet of the recipient in plastic for the duration of the treatment. When paraffin 32 has solidified, and the selected duration of treatment has passed, paraffin 32 is then removed from the hands or feet of the treatment recipient, and remains in the plastic bag for disposal. At the end of the treatment, container 30 may be removed from reservoir 16 by grasping upper edge 34 of container 30. In a preferred embodiment, container 30 is disposable and may then be discarded.

In another embodiment, (a single-serving paraffin charge 40 is used in a single-serving paraffin treatment system 10 having a heating unit 12 with a reservoir 16 as shown generally in FIG. 2. Disposable container 30 contains a paraffin mass 32. In a preferred embodiment, paraffin mass 32 weighs between approximately 3 ounces and 6 ounces. In another embodiment, an upper edge 42 of container 30 extends above reservoir 16 to facilitate insertion and removal of container 30 in reservoir 16. A lid 44 removably seals against upper edge 42 of container 30. In this embodiment, paraffin mass 32 is sealing contained with container 30, and is thus suitable for both shipping and end use by removal of lid 44. For example, a heat-sensitive adhesive 54 may be applied between lid 44 and upper edge 42 of container 30. Alternatively, lid 44 is coated with a varnish-type coating 56 that when heated becomes sticky and seals against upper edge 42 of container 30.

The inventors have tested various container configurations and materials to determine melt times and container strength. These tests have had the results shown in Table 1 below.

| Container | Paraffin | Melt Time | Soak Temperature |
| --- | --- | --- | --- |
| Double wall | 4 ounces | 2 hours, 50 minutes | 152° F. |
| Single wall | 4 ounces | 1 hour 45 minutes | 163° F. |

While this invention has. been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

We claim:

1. A single-serving paraffin treatment system comprising:
   a heating unit having a reservoir;
   a container insertable into the reservoir;
   a paraffin mass weighing less than approximately 6 ounces located in the container; and,
   a brush.

2. The single-serving paraffin treatment system in accordance with claim 1, wherein the container is disposable.

3. The single-serving paraffin treatment system in accordance with claim 1, wherein the container further comprises:
   an upper edge extending above the heating unit when the container is located in the reservoir.

4. The single-serving paraffin treatment system in accordance with claim 1, wherein the paraffin mass weighs approximately between 3 ounces and 6 ounces.

5. The single-serving paraffin treatment system in accordance with claim 1, wherein the brush has a plurality of bristles made of goat hair.

6. The single-serving paraffin treatment system in accordance with claim 1, wherein the brush has a plurality of bristles made of pony hair.

7. A single-serving paraffin charge for use in a single-serving paraffin treatment system having a heating unit with a reservoir, comprising:
   a disposable container insertable into the reservoir;
   a paraffin mass located in the container; and,
   a sealed removable lid attached to the container.

8. The single-serving paraffin charge in accordance with claim 7, wherein the container further comprises:
   an upper edge that extends above the heating unit when the container is located in the reservoir.

9. The single-serving paraffin charge in accordance with claim 7, wherein the paraffin mass weighs approximately between 3 ounces and 6 ounces.

10. The single-serving paraffin charge in accordance with claim 7, further comprising:
    a seal between the lid and the container.

11. The single-serving paraffin charge in accordance with claim 7, wherein the seal is a heat sensitive adhesive.

12. The single-serving paraffin charge in accordance with claim 7, wherein the lid is attached to the container by a threaded connection.

13. The single-serving paraffin charge in accordance with claim 7, wherein the container is made of a polyvinyl-chloride (PVC) material.

14. The single-serving paraffin treatment system in accordance with claim 7, wherein the container is made of a polypropylene material.

15. The single-serving paraffin treatment system in accordance with claim 7, wherein the container further comprises:
    a first container wall; and,
    a second container wall; and,
    at least one circumferential interface between the first wall and the second wall.

16. A single-serving paraffin treatment system comprising:
    a heating unit having a reservoir;
    a disposable container insertable into the reservoir;
    a removable lid sealingly attached to the container;
    an adhesive between the lid and the container;
    a paraffin mass located in the container, weighing less than approximately 6 ounces; and, a brush.

17. The single-serving paraffin charge in accordance with claim 11, wherein the heat sensitive adhesive is a varnish.

18. The single-serving paraffin charge in accordance with claim 7, wherein the seal is a pressure-sensitive adhesive.

* * * * *